United States Patent
Golz-Berner et al.

(10) Patent No.: US 9,446,084 B2
(45) Date of Patent: Sep. 20, 2016

(54) USE OF FREE RADICAL SCAVENGERS FOR PROTECTING AND TREATING SKIN AND HAIR DAMAGES CAUSED BY CHEMOTHERAPY

(75) Inventors: Karin Golz-Berner, Monaco (MC); Leonhard Zastrow, Monaco (MC)

(73) Assignee: Coty Prestige Lancaster Group GmbH, Mainz (DE)

( * ) Notice: Subject to any disclaimer, the term of this patent is extended or adjusted under 35 U.S.C. 154(b) by 0 days.

(21) Appl. No.: 13/035,703

(22) Filed: Feb. 25, 2011

(65) Prior Publication Data

US 2011/0151009 A1    Jun. 23, 2011

Related U.S. Application Data

(63) Continuation of application No. 11/913,501, filed as application No. PCT/EP2006/062076 on May 4, 2006, now abandoned.

(30) Foreign Application Priority Data

| May 4, 2005 | (DE) | ......................... 10 2005 021 804 |
| May 18, 2005 | (DE) | ......................... 10 2005 023 497 |

(51) Int. Cl.
| A61K 36/24 | (2006.01) |
| A61K 9/00 | (2006.01) |
| A61K 36/232 | (2006.01) |
| A61K 36/48 | (2006.01) |
| A61K 36/74 | (2006.01) |
| A61K 36/82 | (2006.01) |
| A61K 38/17 | (2006.01) |
| A61K 38/44 | (2006.01) |
| A61K 45/06 | (2006.01) |

(52) U.S. Cl.
CPC ............. *A61K 36/24* (2013.01); *A61K 9/0014* (2013.01); *A61K 36/232* (2013.01); *A61K 36/48* (2013.01); *A61K 36/74* (2013.01); *A61K 36/82* (2013.01); *A61K 38/17* (2013.01); *A61K 38/446* (2013.01); *A61K 45/06* (2013.01)

(58) Field of Classification Search
None
See application file for complete search history.

(56) References Cited

U.S. PATENT DOCUMENTS

| 5,403,834 A | 4/1995 | Malfroy-Camine et al. |
| 5,633,285 A | 5/1997 | Martin |
| 5,962,018 A * | 10/1999 | Curtis .................. A61K 9/1635 424/450 |
| 6,060,083 A * | 5/2000 | Dorr et al. .................... 424/450 |
| 2003/0022867 A1 | 1/2003 | Stogniew et al. |

FOREIGN PATENT DOCUMENTS

| DE | 4241154 | 3/1994 |
| DE | 10325156 | 12/2004 |
| EP | 1308154 A2 * | 5/2003 |
| EP | 1217984 | 12/2004 |
| JP | 2002003389 | 1/2002 |
| WO | 9503061 | 2/1995 |
| WO | 9844895 | 12/1998 |
| WO | 9966881 | 12/1999 |
| WO | WO 0126617 A1 * | 4/2001 |
| WO | 03013245 A1 | 2/2003 |
| WO | 2005014524 A2 | 2/2005 |
| WO | 2005016272 A2 | 2/2005 |

OTHER PUBLICATIONS

Farr et al. Case Rep Oncol 2011;4:229-235.*
Lorusso et al. Annals of Oncology Advance Access (2007) 1-6.*
Alvarez-Lorenzo et al., "Intersupplier and interlot variability in hydroxypropyl celluloses: Implications for theophylline release from matrix tablets", Pharmaceutica Acta Helvetiae (Jan. 28, 1998) 73: 113-120.

* cited by examiner

*Primary Examiner* — Amy L Clark
(74) *Attorney, Agent, or Firm* — Schwegman Lundberg & Woessner, P.A.

(57) ABSTRACT

One or more free radical scavengers are used as prophylactically or therapeutically effective substances amd microparticles having an average particle size ranging from 5 to 200 μm for the preaparation of a topuical pharmaceutical compostion for the protection or treatment of skin or hair damages caused buy chemotherapeutic treatment. The invention also concerns a method for the protextion or treatmnent of skin or hair damages of a mammal caused by chemotherapy. A kit for the protextion or treatment of hair damages caused by chemotherapeutic treatment consists of a topical composition including microparticles together with the free radical scavengers and a shampoo for an effective hair cleaning and supporting the hair treatment. A kit for the protection or treatment of skin damages caused by chemotherapy consists of a topical composition including microparticles together with free radical scavengers and a cleansing milk for an effective skin cleaning and supporting the skin treatment.

11 Claims, No Drawings

USE OF FREE RADICAL SCAVENGERS FOR PROTECTING AND TREATING SKIN AND HAIR DAMAGES CAUSED BY CHEMOTHERAPY

CROSS-REFERENCE TO RELATED APPLICATIONS

The present application is a continuation of U.S. patent application Ser. No. 11/913,501 now abandoned, filed Jun. 24, 2008. Said application is expressly incorporated herein by reference in its entirety.

The present invention relates to the use of one or more free radical scavengers as prophylactically or therapeutically effective substances and microparticles having an average particle size ranging from 5 to 200 µm for the preparation of a topical pharmaceutical composition for the protection or treatment of skin and/or hair damages caused by chemotherapeutic treatment.

The invention also concerns a method for the protection or treatment of skin and hair damages of a mammal caused by chemotherapy. The invention further relates to a kit for the protection or treatment of hair damages caused by chemotherapeutic treatment consisting of a topical composition comprising microparticles together with free radical scavenger and a shampoo for an effective hair cleaning and supporting the hair treatment. A kit for the protection or treatment of skin damages caused by chemotherapy consisting of a topical composition comprising microparticles together with free radical scavengers and a cleansing milk for an effective skin cleaning and supporting the skin treatment is a further object of the present invention.

When carcinogenic diseases are treated, the use of chemotherapeutic substances is widespread when combating tumour cells and pathogens such as viruses and fungal infections as part of so-called chemotherapy or cytostatic therapy treatment. Chemotherapy is used, among other things, with acute or chronic leukaemia, malignant lymphomas or other tumours in the intestine, lung, breast and other organs. Different medications are used, depending on the type of illness and the condition of the patient. Cytostatic agents which are frequently used in chemotherapy and which cause severe side effects are for instance the anthracyclines. They include daunorubicin (Cerubidine), doxorubicin (Adriamycin, Rubex), epirubicin (Ellence, Pharmorubicin), and idarubicin (Idamycin).

The occurrence of acute or long-term side effects, or side effects which occur later in connection with the chemotherapy, including side effects to the skin and mucous membranes of patients, is generally known. A further consequence of chemotherapy treatment is also increased sensitivity to herpes viruses or fungal infections.

The side effects to skin include dry or scaly skin, itchy skin swellings, red patches, the formation of blisters, skin lesions with low-level mechanical impacts, allergies, skin discoloration along the infusion veins, pigment spots, hand and foot syndrome (PPE) etc.

Aside from the treatment by medication of skin in medium and severe cases (e.g. in the case of shingles with virustatica), patients are usually simply advised to avoid mechanical irritants by wearing suitable clothing, avoiding cosmetic preparations with allergy potential, or to use dermatological treatments which soothe the skin, such as calendula cream. These procedures are frequently not satisfactory.

Furthermore, it is known that chemotherapy is frequently accompanied by a temporary partial or total loss of hair, in particular of head hair (Alopecia), which can lead to severe psychological damage, particularly among women.

It is therefore object of the present invention significantly to reduce or completely to prevent skin and hair damages during chemotherapeutic treatment.

The object of the present invention is solved by a topical pharmaceutical composition which is applied prior, during and/or subsequent to chemotherapeutic treatment to the concerned skin or scalp areas of the mammal, this composition comprising one or more free radical scavengers as prophylactically or therapeutically effective substances and microparticles having an average particle size ranging from 5 to 200 µm as carrier materials.

It was found that chemotherapeutic substances which are administered systemically or intravenously quickly penetrate from inside-out onto the skin via sweat, and are distributed homogeneously over the skin surface by lateral spreading. Then they penetrate the skin from outside in the same manner as topically applied substances. The concentration of the systemically and intravenously applied substances correlates in terms of time with the concentration of these substances in the blood. The highest concentration of chemotherapeutic substances on the skin was observed in places where a high concentration of sweat glands occurs, e.g. on the forehead, the axilla, and the balls of the hands and feet. The majority of skin irritations also occur here. Without wishing to be bound by theory, it is believed that this appears to be the reason for the formation of PPE.

Furthermore, it was found that chemotherapeutic substances frequently accumulate in the hair follicles. They are in part expelled there together with the extruded fat from the sebaceous gland, and this coincides with a rapid loss of hair during a chemotherapeutic treatment.

Now it was found that the occurrence of side effects from chemotherapeutic substances on the skin or on the hair can be prevented or significantly reduced when antioxidation agents or such substances which are known as radical scavengers can be effective on the skin prior, during or subsequent to chemotherapy together with microparticles. Obviously, to ensure an effective protection or treatment it seems to be necessary to neutralize the free radicals on the skin or scalp surface before they penetrate the skin from outside again and are stored there over a long period of time causing the above described side effects. For this, according to the invention, the free radical scavengers and antioxidation agents have been administered together with microparticles having an average particle size from 5 to 200 µm to ensure the neutralization of the free radicals on the skin or scalp surface before they penetrate the skin from outside again. "Side effects to the skin", "skin side effects" or "skin damages" are understood as being all the effects described in the introduction, together with further side effects which are not explicitly listed, but which are generally known, such as those named in the "Schweizerische Rundschau für Medizin" 91 (2002) no. 24, p. 1063-1087. "Hair side effects" or "hair damages" are understood as being the full or partial loss of body hair, in particular of head hair, hair brittleness, hair discoloration, loss of hair colour and similar other effects.

The term "applying topically" also includes application to the mucosa, especially of the head and neck region.

Chemotherapeutic treatment is understood as being the systemic or intravenous dosage of pharmaceutical, synthetic or microbiologically manufactured products, or products isolated from a mixture, which are suitable for use as anti-cancer agents. Stem cell transplants are regarded as being equivalent to this treatment, which can lead to similar effects on the skin. Chemotherapeutic substances of this nature include Fluoruracil, Fluordesoxyuracil, Leucovorin, Taxol, Gemzur, Doxorubicin and those named for example in the "Schweizerische Rundschau für Medizin" 91 (2002) no. 24, p. 1078ff. Chemotherapeutic substances which lead to hand and foot syndrome include in particular Vinorelbin, Methotrexat and Etoposide.

According to one embodiment of the invention, scavengers which a high capacity for capturing free radicals are used in the topical preparation, whereby the radical protection factor of the preparation constitutes at least $85 \times 10^{14}$ radicals per mg of preparation, measured by determining the number of free radicals of a solution of a test substance ($S_1$) using electron spin resonance (ESR) in comparison with the ESR measurement result of the preparation according to the ratio $$RPF=(RC \times RF)/PI$$

whereby $RF=(S_1-S_2)/S_1$; RC=the concentration of the test substance (radicals/ml); PI=the concentration of the active substance preparation (mg/ml). $S_2$=signal amplitude of the antioxidant.

The radical protection factor (RPF) gives the activity for the binding of free radicals by antioxidation agents or scavengers against a test substance. According to the invention, all generally known enzymatic and non-enzymatic antioxidants can be used as free radical scavengers, insofar as they can be formulated to a topical preparation and comprise a corresponding radical protection factor.

The antioxidants used are selected, for example, from the group of vitamins consisting of tocopheroles and their derivatives, in particular α-tocopherole or α-tocopherylester, in particular tocopherylacetate, tocopherylacylate, -laurate, -myristate, -palmitate, -oleate or -linoleate; vitamin A and its derivatives, in particular retinyl palmitate; vitamin C and its derivates, in particular isoascorbate, (2- or 3- or 6-) o-alkylascorbic acids, ascorbic acid ester, such as ascorbyl acetate, ascorbyl phosphate, 6-o-lauroyle-, myristoyle-, palmitoyle-, oleoyle- or linoleoyle-L-ascorbic acid; folic acid and its derivatives.

Further scavengers which can be used according to the invention have been selected from the group consisting of flavonoids, comprising flavons, flavonols, flavanonals and chacons, in particular citrus flavonoids such as rutin, naringin and neohesperidin; carotinoids and carotines such as α-carotine and β-carotine; α-lipon acid, lipon acid amide; amino acids such as histidine, glycine, tyrosine, tryptophane and amino acid derivatives; α-hydroxy acids such as citron acid, milk acid, apple acid; uric acid and its derivatives; rutin acid, α-glucosylrutine; phenolcarbon acids such as rosemary acid or ferula acid; humin acid; gallic acid and gallic acid derivatives such as methyl-, ethyl-, propyl-, amyl-, butyl- and laurylgallate; gallic extracts; unsaturated fatty acids; ubichinon, ubichinol; zinc and its salts; selenium compounds; coenzyme Q10; urocanin acid; lecithin; anthocyanes; polyphenolenes; tetrahydrodiferuloylmethane (THC).

Preparations from plant extracts with a high radical protection factor (designed as RPF complex) are described in WO 99/66881, WO 01/26617 and DE 103 25 156 A1 (which disclosures are incorporated herein by reference). These preparations can also be used in the present invention as antioxidants.

Further advantageous plant extracts which are useful as free radical scavengers in the present invention are acerola extract, citrus peel or leaf extracts (*Citrus bigaradia, Citrus hystrix, Citrus aurantifolia, Citrofortunella microcarpa, Citrus aurantium, Citrus reticulata*), bitter orange extract (peel or fruit), cherry extract from Spanish cherries, kiwi extract (*Actinidia chinensis*), papaya fruit extract (*Caricae papayae*), tea extract [leaves from green or black tea, leaves or bark from New Jersey tea (*Ceanthus velutinas*)], coffee bean extract from green or roasted beans, prunus extract, e.g. from *Prunus armeniaca, Prunus dulcis, Prunus persica, Prunus domestica, Prunus spinosa, Prunus serotina, Prunus virginiana*, extracts from the bark of the Mexican skin tree (*Mimosa tenuiflora*), angelica root extract (*Angelica archangelica*), *Pongamia pinnata* extract, and tomato extract.

The amount of these plant extracts in the topical preparation can preferably be between 0.05 and 45 weight %, preferably 0.1 to 40 weight %, in particular 1.5 to 20 weight %, whereby mixtures of these extracts can also be contained in the effective substance preparation. The concentration depends on the radical protection factor of the extract or scavenger. In this way, extracts with very high radical protection factors of between 10000 and 90000 can be contained in relatively low concentrations of 0.1 weight %, insofar as they maintain the corresponding RPF over longer periods of time of several weeks to several months.

Specifically preferred are content levels of scavengers in the topical composition of 3-33 weight %, in particular 9-26 weight %, relating to the total weight of the composition.

The radical protection factor of the preparation advantageously constitutes at least $110 \times 10^{14}$ radicals per mg of preparation, preferably at least $300 \times 10^{14}$ radicals per mg of preparation, in particular at least $500 \times 10^{14}$ radicals per mg.

Embodiments of the invention in which the radical protection factor of the preparation is between 200 and $12000 \times 10^{14}$ radicals per mg of preparation are specifically preferred.

The concentration of the radical scavenger or radical scavenger mixture of about 1 to about 40 weight % is preferred.

Particularly preferred is a mixture of plant extracts (RPF complex III), consisting of between 0.1 and 2 weight % extract of green coffee beans, between 0.1 and 2 weight % extract of leaves of *Camellia sinensis*, between 0.1 and 2 weight % extract of *Pongamia pinnata* and between 0.1 and 2 weight % extract of the roots of *Angelica archangelica* and the rest of up to 100 weight % from a single-value $C_2$-$C_5$ alcohol. The extract mixture is free of liposomes, and has a radical protection factor in the region of $1400-2900 \times 10^{14}$ radicals per mg. This extract mixture can preferably be contained in a proportion of between 8 and 25 weight %, preferably between 10 and 15 weight %, in a preparation according to the invention in relation to the total weight of the preparation.

A further preferred scavenger is the RPF complex I from WO99/66881 as mentioned above (e.g. from example 1 or 2) or WO 01/26617. This consists of an effective substance preparation containing a product gained from the extraction of the bark of Quebracho blanco and the subsequent enzymatic hydrolysis, which contains at least 90 weight % proanthocyanidin oligomers and a maximum of 10 weight % of gallic acid, in microcapsules, and a silkworm extract gained from extraction, which contains the peptide cecropine, amino acids and a vitamin mixture, and a non-ionic, cationic or anionic hydro-gel or a mixture of hydro-gels, and one or more phospholipids and water (RPF 2400), where appropriate supplemented by cyclodextrine and a yeast digest described later (RPF 4800).

An advantageous scavenger is also a mixture of enzymes and vitamins, specifically a digest from a yeast produced by ultrasound treatment, whereby the digest contains SOD, protease, vitamin $B_2$, vitamin $B_6$, vitamin $B_{12}$, vitamin $D_2$ and vitamin E. Preferably, it contains at least 150 U/ml SOD, protease and vitamins B and D, whereby the ratio SOD:protease as international units lies at least in the region of between 3:1 and 8:1 (RPF 2020×10$^{14}$ radicals/mg). The enzyme/vitamin mixture is produced using an extraction method using ultrasound, which is described in DE 4241154C1, and in which a cell dispersion or suspension is passed through an ultrasound area in an ultrasound through-flow cell, in which the sonotrode protrudes into the through-flow cell up to between half and two-thirds of its length, and is immersed into the medium to be acoustically irradiated. Here, the sonotrode has an angle of 80.5 to 88.5°, and the ratio between the immersion length of the sonotrode in mm to the acoustic irradiation volume in ml is set at between 1:1.1 and 1:20. The proportion of solid substances in the medium to be acoustically irradiated is in the region of between 1:0.02 and 1:2.2 (weight %).

Yeasts such as baker's yeast, brewer's yeast, wine yeast and specially treated yeasts, such as SOD-enriched yeasts, can be used as the cell dispersion.

A cell dispersion which can advantageously be used contains e.g. *Saccharomyces cerevisia*.

The addition of e.g. 1-10 weight % of a yeast digest of this nature from baker's yeast or organic yeast can synergetically increase an already present radical protection factor from another oxidation agent.

Further preferred radical scavengers include (in brackets are the RPF values without the addition "×10$^{14}$ radicals/mg") tomato extract (1000); carrot extract (300); RPF complex+vitamin E in cyclodextrine (7200); stabilised vitamin C (8290); an ultrasound yeast digest from baker's yeast (2020); rape extract (67000); RPF complex I in cyclodextrines (720); oregano oil (Origanox) (90306); *Origanum vulgare* extract (80000); tannic acid (310000); pine bark extract (12500); Himothatus sucruba extract (700); Emplica® (Merck) (42400); grape skin, white (53000); grape skin, red (95100); flavonoid extract from red wine (6000); rosemary acid (36000-68000); curry extract (12500); saffron extract (900); orange peel extract (24000); rape oil (2550); strawberry oil (1300); green tea extract (21500); grapefruit extract (53000); natrium-ascorbyl-phosphate (35000); edelweiss extract (15500); *Camellia sinensis* extract (840).

According to the invention the topical composition comprises microparticles with an average size of from 5 to 200 μm, preferably from 5 to 100 μm, more preferred from 5 to 50 μm and especially preferred from 8 to 40 μm. Without wishing to be bound by theory the particle size seems to be important to prevent the penetration of microparticles carrying the free radical scavengers into the skin and/or to prevent the penetration of microparticles carrying the chemotherapeutic substances they may have caught into the skin.

In a preferred embodiment of the invention the microparticles are selected from porous materials, cyclodextrins or mixtures thereof. The porous materials are preferably selected from the group consisting of ground natural organic compounds such as for instance ground fixed algae or horny sponges, ground plants or parts thereof such as for instance bamboo powder, grain starches, pigments, iron oxides, silicates, mica, kaolin, clays containing manganese, white clay, silica gel calcium carbonate, talcum, bismuth-oxychloride, activated carbon, ceramic particles, $SiO_2$, ZnO, $SrO_2$, $TiO_2$ or mixtures thereof. Especially preferred for the purpose of the present invention are horny sponges, preferably horny sponges of types Euspongia officinalis, Spongia usitatissima, Hippospongia equina or mixtures thereof, bamboo powder, kaolin, white clay, $SiO_2$, calcium carbonate, silica gel, silicates, activated carbon or mixtures thereof.

Preferred cyclodextrins according to the invention are β-or γ-cyclodextrins. The microparticles of the invention are commercially available or easily obtainable as it is well known in the prior art.

The concentration of the microparticles in the composition ranges from 0.1 to 10% by weight, relating to the total weight of the composition, preferably 0.6 to 8% by weight, more preferred 1 to 6% by weight.

According to one embodiment of the invention the topical composition can be prepared by soaking the microparticles with an aqueous solution or emulsion of the corresponding free radical scavenger(s) and adding this phase by stirring slowly (50-200 rpm) at room temperature (18-25° C.) to the auxiliary substances and further components necessary for the formulation of a topical composition.

The compositions of the invention may contain, alongside the scavengers and the microparticles, other dermatological auxiliary substances, as are commonly used in preparations of this type, such as water, preservation agents, colorants, thickening agents, moistening substances, alcohols, polyols, electrolytes, gel-forming substances, polar and non-polar oils, polymers, copolymers, emulsifying agents and stabilisers. In a preferred embodiment of the invention, the topical preparations contain stabilisers for the antioxidants.

In order to apply the scavengers topically, they are formulated in the usual way with auxiliary substances to solid formulations which can be applied to the skin, such as creams, gels, salves or emulsions, or to liquid formulations which can be applied to the skin, such as solutions, suspensions, lotions, sera or oils.

Transdermal systems can also be used as topical preparations, such as adhesives, plasters or bandages, which contain the antioxidants together with the microparticles.

Advantageous therapeutic preparations are also aqueous systems in the form of tinctures (e.g. for the mucosa) or dry substances which are designed for the preparation of baths (bath concentrates).

A further component the preparation can contain are finely distributed, hard magnetic mono-area particles (monocrystals) with a high coercitive field force of 3000 to 5000 Oerstedt and with grain sizes in the region of between 50 and 900 nm, preferably 50-250 nm, whereby these hard magnetic particles are in particular barium and/or strontium hexaferrites, produced using glass crystallisation technology by cultivating monocrystals from a quenched glass melt (see WO95/-03061 e.g. example 2 or 3; and WO98/44895 e.g. example 1C). The proportion of monocrystals can be between 0.1 and 5 weight %.

The preparation according to the invention can furthermore contain moisturising agents such as glycerine, butylenglycol, propylenglycol or mixtures of these.

The oils used in the topical preparation according to the invention can be standard cosmetic oils such as mineral oil, hydrogenated polysobutene, squalane produced synthetically or from natural products, cosmetic esters or ethers which can be branched or non-branched, saturated or unsaturated, plant oils, or mixtures of two or more of these. Particularly suitable oils are for example silicon oils, mineral oils, hydrogenated polyisobutene, polyisoprene, squalane, tridecyltrimellitate, trimethyl-propane-triisostearate, isodecylcitrate, neopentylglycol-diheptanoate, PPG-15-stearylether and plant oils such as calendula oil, jojoba oil, avocado oil, macadamia nut oil, olive oil, castor oil, cocao butter, coconut oil, maize oil, cotton seed oil, olive oil, palm kernel oil, rape seed oil, saflor oil, sesame seed oil, soja bean oil, sunflower seed oil, wheatgerm oil, grape seed oil, kukui nut oil, thistle oil and mixtures of these.

Depending on which oils are selected, the dermatological properties of the fixed composition are affected, such as the degree of transparency, the softness, hardness and spreading properties.

The preparations according to the invention can be O/W or W/O emulsions. Suitable emulsifying agents for O/W emulsions are for example adsorption products from 2-30 Mol ethyl oxide on linear $C_8$-$C_{22}$ fatty alcohols, on $C_{12}$-$C_{22}$ fatty acids and on $C_8$-$C_{15}$ alkyl phenoles; $C_{12}$-$C_{22}$ fatty acid mono and diesters from adsorption products from 1-30 Mol ethyl oxide on glycerine.

Suitable emulsifying agents for W/O emulsions are for example adsorption products from 2-15 Mol ethyl oxide on castor oil, ester from $C_{12}$-$C_{22}$ fatty acids and glycerine, polyglycerine, pentaerythrite, sugar alcohols (e.g. sorbitol), polyglucosides (e.g. cellulose); polyalkyl-glycols; wool fat alcohols; copolymers of polysiloxan-polyalkylpolyether.

As has already been described, the radical protection factor (RPF) determines the activity of a substance for binding free radicals against a test substance. This test substance consists of a highly reactive, semi-stable radical which reacts with all known antioxidation agents. Such radicals include nitroxides such as proxo (2.2,5.5-tetramethyl-1-dihydropyrrolinoxy-nitroxide), tempol (2.2,6.6-tetramethyl-1-piperidinoxy-4-ol-nitroxide), DTBN (di-tert-butyl-nitroxide or preferably DPPH (1.1-diphenyl-2-picrylhydrazyl.

The RPF is measured in such a way that the signal amplitudes of the test radical created by electron spin resonance (ESR/EPR) are measured before and after mixing with an antioxidation agent/scavenger, and the RPF is calculated from this. The RPF is known for a series of standard antioxidation agents; for all-trans-retinol it is 827, for all-trans-retinolacetate, 196; for DL-$\alpha$-tocopherol it is 41200 and for $\alpha$-tocopherylacetate, it is 48, in each case $\times 10^{14}$ radicals/mg.

The precise measuring procedure for the radical protection factor has been described by Herrling, Groth, Fuchs and Zastrow in Conference Materials "Modern Challenges To The Cosmetic Formulation" 5.5.-7-5.97, Düsseldorf, p. 150-155, Verlag f. chem. Ind. 1997. Here, based on the known concentration of the test substance (here: DPPH) or the number of its free radicals (radicals per ml), a signal amplitude $S_1$ is measured using an ESR spectrometer. The test radical is dissolved in the same way as the antioxidation agent in a (e.g. 0.1 m) water/alcohol solution. Then the signal amplitude $S_2$ of the antioxidation agent is measured. The normalised difference between the two signal amplitudes is the reduction factor RF $$RF=(S_1-S_2)/S_1.$$

The result of the radical reduction of the test substance RC×RF is normalised in relation to the quantity of the product input PI (mg/ml). Here, the RC is the quantity of the test substance, i.e. the known number of radicals in the test substance. The radical protection factor is calculated according to the following equation:

$$RPF = \frac{RC\,[\text{radicals/ml}] \times RF}{PI\,[\text{mg/ml}]}$$

The result is:

$$RPF = N \times 10^{14}\,[\text{radicals per mg}],$$

whereby N is a positive, real figure and the RPF can be reduced to the abbreviated numerical value N. This abbreviation is used in the examples of the present invention.

The radical protection factor can be determined using an ESR spectrometer (GALENUS GmbH, Berlin, Germany), and is a value for labelling products with regard to their ability to bind free radicals. The procedure is an in-vitro procedure, in which no individual properties of the user influence the antioxidants.

By adding cyclodextrines, which have a radical protection factor of 0, a further increase of this factor of 1.3 to 10 times can surprisingly be observed. Standard $\alpha$-, $\beta$-, or $\gamma$-cyclodextrines (Wacker-Chemie) or mixtures of these can be used as cyclodextrines. Cyclodextrines are known as encapsulation materials for effective pharmaceutical and cosmetic substances, and can therefore also be used here for encapsulating scavengers.

The invention also relates to the use of scavenger substances for the protection or treatment of hair loss, especially alopecia, as a side effect of chemotherapy. When hair, in particular head hair, is treated simultaneously during the chemotherapy with a mixture which comprises at least one RPF of between 100 and 10000×$10^{14}$, preferably 100-2600×$10^{14}$ radicals per mg of the treatment preparation, the anticipated hair loss does not occur, or only occurs to a limited degree. A particularly preferred scavenger for the protection or treatment of hair damages is an aqueous extract of walnut or hazelnut leaves.

The use of scavenging substances is preferably achieved as a hair pack, hair gel, hair water, hair emulsion, hairspray, hair lather, protein pack, hair structure, vitaliser, combing aid or any other suitable form. This is applied fresh to the hair at least twice daily, in particular, 3-5 times daily. For hair packs or hair treatments, the product is left on the scalp and hair for at least 1 to 2 hours before being rinsed out. It is also possible to leave the hair packs one or more days on the scalp.

The hair treatment is conducted prior to, simultaneously, or subsequent to the chemotherapy treatment, and preferably at least 6 to 7 days following the chemotherapeutic treatment, in particular for 14 to 60 days afterwards or until the next treatment with the cytostatic agent.

The use of the preparation according to the invention is supported by an additional massage at the site where the preparation is applied, in particular a massage of the scalp, preferably 5 to 10 minutes.

The invention also relates to a method for the protection or treatment of skin and hair damages of a mammal caused by chemotherapeutic treatment comprising topically administering to the concerned skin and scalp areas of the mammal a prophylactically or therapeutically effective amount of one or more free radical scavengers which are administered in the form of a topical pharmaceutical composition comprising microparticles having an average particle size ranging from 5 to 200 μm.

The skin damages which are treated according to the invention are for instance the palmar-plantar erythrodysaesthesia syndrome (PPE), erythema and dry skin.

A severe side effect of chemotherapeutic treatment to the hair is alopecia. According to the invention the topical composition is administered to the concerned skin and/or scalp areas prior to, during and/or subsequent to chemotherapeutic treatment with cystostatic agents, preferably 1 day prior to chemotherapeutic treatment, during the treatment and at least 6 to 7 days after the chemotherapeutic treatment, preferably 14 to 60 days afterwards or until the next treatment with the cytostatic agent. The topical composition should be administered to the concerned skin or scalp area at least twice daily, preferably 3-5 times daily, in an amount of at least 2 mg/cm$^2$, preferably of 2 to 10 mg/cm$^2$.

A kit for the protection or treatment of hair damages caused by chemotherapeutic treatment consisting of
a) a topical composition comprising one or more free radical scavengers and microparticles having an average particle size ranging from 5 to 200 µm, wherein the concentration of the radical scavenger(s) in the composition ranges from 0.05 to 45% by weight, and the concentration of the microparticle(s) in the composition ranges from 0.1 to 10% by weight and
b) a shampoo comprising a free radical scavenger up to 2% by weight of the total weight of the shampoo is a further object of the present invention. In a preferred embodiment the radical protection factor $R_F$ of the topical composition of this kit should be at least $85 \times 10^{14}$ radicals/mg composition.

The invention also concerns a kit for the protection or treatment of skin damages caused by chemotherapeutic treatment consisting of
a) a topical composition comprising one or more free radical scavengers and microparticles having an average particle size ranging from 5 to 200 µm, wherein the concentration of the radical scavenger(s) in the composition ranges from 0.05 to 45% by weight, and the concentration of the microparticle(s) in the composition ranges from 0.1 to 10% by weight and
b) a cleansing milk comprising a free radical scavenger up to 2% by weight of the total weight of the cleansing milk. In a preferred embodiment the radical protection factor $R_F$ of the topical composition of this kit should be at least $85 \times 10^{14}$ radicals/mg composition.

A further object of the present invention is the use of one or more free radical scavenger(s) as prophylactically or therapeutically effective substances for the preparation of a topical pharmaceutical composition for the protection or treatment of skin and hair damages caused by chemotherapeutic treatment and a method for the protection or treatment of skin and hair damages of a mammal caused by chemotherapeutic treatment comprising topically administering to the concerned skin and scalp areas of the mammal a prophylactically or therapeutically effective amount of one or more free radical scavengers which are administered in the form of a topical pharmaceutical composition.

The invention will now be explained with reference to examples. All data is given as a weight percentage, insofar as no other information is given.

EXAMPLE 1

Anti-Radical Cream I

Phase A
 Isopropylmyristate 3.0; steareth-2 2.3; steareth-21 1.5; PPG-15 stearylether 3.0
Phase B
 Water q.s. ad 100; EDTA 0.04; carbomere 0.3; Water/NaOH 0.3; glycerine 2.0; kaolin 0.1 (particle size 5-50 µm); bamboo powder 0.5 (particle size 5-50 µm)
Phase C
 Dimethicone 2.0
Phase D
 Conservation agent 0.1
 β-carotine 5.0

The separately prepared phases A and B are heated to 75° C. and combined by stirring. Phase C is added to the mixture by stirring and it is cooled to approximately 40° C. Phase D is added by stirring at 35° C. and the mixture is homogenised.

$RPF = 1270 \times 10^{14}$ rad./mg.

EXAMPLE 2

Anti-Radical Cream II

Phases A and C correspond to those in Example 1.
Phase B
 Water q.s. ad 100; EDTA 0.04; carbomere 0.3; Water/NaOH 0.3; glycerine 2.0; horny sponges 1.0 (particle size 5-50 µm); cyclodextrine 0.01
Phase D
 Conservation agent 0.08
 β-carotine 3.0
 RPF-complex I[1]/cyclodextrine 10.0
 Rosemary acid 0.5

[1] according to WO99/66881 (active substance complex according to Example 1)

The preparation corresponds to that in Example 1

$RPF = 3820 \times 10^{14}$ rad./mg.

EXAMPLE 3

Anti-Radical Cream III

Phases A and C correspond to those in Example 1.
Phase B
 Water q.s. ad 100; EDTA 0.04; carbomere 0.3; NaOH 0.3; glycerine 2.0;
Phase D
 Conservation agent 0.08
 RPF-complex I[1] 5.0

[1] according to WO99/66881 (active substance complex according to Example 1)

Phase E
 horny sponges 2.0 (average particle size 10-40 µm); β-carotine (liquid) 1.5; Rosemary acid (liquid) 0.5

β-carotine and Rosemary acid are mixed. The horny sponges are added to this mixture at room temperature (18-25° C.). For soaking the microparticles it is stirred slowly (50-200 rpm) for about 10 minutes.

Then, the separately prepared phases A, B, C and D are mixed together. Phase E is added at room temperature (18-25° C.) by stirring slowly (50-200 rpm).

EXAMPLE 4

Anti-Radical Cream IV

Phases A and C correspond to those in Example 1.
Phase B
 Water q.s. ad 100; EDTA 0.04; carbomere 0.3; Water/NaOH 0.3; glycerine 2.0; horny sponges 1.0 (particle size 8-40 µm); bamboo powder 0.1 (particle size 8-40 µm); SiO$_2$ 0.2 (particle size 5-50 µm)
Phase D
 Conservation agent 0.09
 RPF-complex I[2] 10.0
 Peel extract of red grape 2.0
 Origanox® WS 1.0
 Vitamin C stabilised 2.0;

The preparation corresponds to that in Example 1

$RPF=6310\times10^{14}$ rad./mg.

[2] according to WO01/26617 (active substance complex according to Example 1)

EXAMPLE 5

Anti-Radical Cream V

Phases A and C correspond to those in Example 1.
Phase B
Water q.s. ad 100; EDTA 0.04; carbomere 0.3; Water/NaOH 0.3; glycerine 2.0; white clay 1.0 (average particle size about 5 µm); kaolin 0.1 (average particle size 50 µm)
Phase D
Conservation agent 0.1
Tomato extract 2.0
Pine bark extract 0.5
RPF-complex 1[1]/cyclodextrine 10.0

[1] according to WO99/66881 (active substance complex according to Example 1)

The preparation corresponds to that in Example 1.

$RPF=4040\times10^{14}$ rad./mg.

EXAMPLE 6

Cleansing Milk

Phase A
Water q.s. ad 100; propylene glycol 3.0; glycerine 2.0; carbomere 0.5
Phase B
cetyl alcohol 3.0; shea butter 0.1 Neutralizer/pH adjuster: Triethanolamine 0.5 Preservative: 2-Bromo-2-nitropropane-1.3-diol 0.1 RPF-complex 111[3] consisting of alcohol denat. (99.2); *Pongamia Pinnata* Seed Extract (0.2); *Angelica Archangelica* Root Extract (0.2); *Camellia Sinensis* Leaf Extract (0.2); *Coffea Arabica*(Coffee) Leaf/Seed Extract (0.2) (The percentages relate to the total weight of the RPF-complex.)

[3] according to the extract mixture of Example 1 of DE 103 25 156 A1

Preparation
Phase A is put in the main vessel and heated up to 45-50° C. The carbomere is slowly added and homogenized totally. Phase A is now heated to 65° C. Phase B is separately heated to 65° C. and stirred until it is homogenous. Then, Phase B is added into Phase A in the main vessel and homogenized well. Stirring is continued. Then it is cooled down to 50-55° C. under stirring. After that the triethanolamine is added and homogenized well. Now, under stirring it is cooled down below 40° C. and the RPF-complex and the preservative agent are added till homogeneity. Cooling to room temperature is continued and parameters such as pH and viscosity are controlled.

EXAMPLE 7

Permanent Hair Rinse

Water q.s. ad 100; carbomere 0.08; triethanolamine 0.08; RPF-complex I[1] (liposomes) 2.0; RPF complex I[2] 2.0; β-carotine 1.0; concentrate of red grape skin 3.0; α-tocopherolacetate 1.0; vitamin C, stabilised 1.5; horny sponges 1.0 (average particle size 40 µm); white clay 0.1 (average particle size 5 µm).

The components are mixed together. The rinse obtained has a RPF of $1630\times10^{14}$ rad./mg.

EXAMPLE 8

Hair Pack I

Water q.s. ad 100; carbomere 2.5; triethanolamine 2.5; Green coffee oil 2.0; rape oil 3.0; oregano oil 2.0; ethanol 4.0; hard magnetic particles 100-300 nm according to WO98/44895 example 1C 0.1; RPF complex I[1] 2.0; RPF complex I[2] 2.0; β-carotine 1.0; concentrate of red grape skin 3.0; birch bark extract 2.0; polyethylene globules 300-900 nm 3.0; bamboo powder 0.01 (particle size 100-200 µm); $SiO_2$ 3.0 (particle size 100-200 µm); white clay 0.01 (particle size about 100 µm); silica gel 0.1 (particle size 100-150 µm).

The components are mixed together. The obtained composition has a RPF of $2410\times10^{14}$ rad./mg.

EXAMPLE 9

Hair Pack II

Water q.s. ad 100; carbomere 2.5; triethanolamine 2.5; Green coffee oil 2.0; rape oil 2.0; calendula oil 2.0; ethanol 4.0; hard magnetic particles 100-300 nm according to W098/44895 example 1C 0.1; Yeast extraction product from baker's yeast according to DE 4241154 Cl 2.2; Pine bark extract 2.0; silica gel 2.7(average particle size 5 µm); horny sponges 0.5(particle size 50-80 µm); kaolin 0.1(particle size 100-200 µm); bamboo powder 0.5(average particle size 100 µm); activated carbon 0.01(particle size 150-200 µm). The preparation is conducted as described in example 7; RPF=$2590\times10^{14}$ rad./mg.

EXAMPLE 10

Shampoo $H_2O$ q.s. ad 100; RPF I[1] 1.0; Sodium Chloride 0.1; Fragrance 1.2; Preserving Agent 0.8; Sodium Hydroxide (10%) 0.5.

The components are mixed at room temperature (part A).
D-Panthenol 0.2; Tocopherol acetate 0.5; Propylene Glycol 2.0; Sodium Laureth Sulfate 15.00; TEA-Lauryl Sulfate 10.00; Quaternium 80/Propylene Glycol 3.0; Citric Acid 0.09; Cocamidopropyl Betaine 10.00. The components are mixed at room temperature and added to part A.

EXAMPLE 11

Protection of PPE

The creme of Example 1 was administered to 8 femal cancer patients who had to be treated with doxorubicin for 6 months. The administration of the creme was started one day before the first treatment with doxorubicin. This day each patient was creamed on the palm and plantar areas in the morning and in the evening. Next day, the day of the chemotherapy, each patient was creamed in the morning and in the evening and two times during the day. Starting with the first day after the treatment with doxorubicin each patient was creamed each day in the morning and in the evening for at least 6 or 7 days, preferably until the next treatment with doxorubicin. In general, before each repeated administration of the creme the concerned areas have been cleaned with the cleansing milk of Example 6. Non of the 8 patients developed a PPE.

By comparison, three patients who had to be treated with doxorubicin for 6 months received the creme of Example 1 without the carrier particles (bamboo powder and kaolin) prior, during and subsequent to the chemotherapeutic treatment according to the above described regimen. These three patients developed a low-level PPE which revealed in erythemas.

Two further female cancer patients were treated according to the above described regimen with the creme of Example 1 without free radical scavengers and without carrier particles. These two patients developed a strong PPE.

EXAMPLE 12

Treatment of PPE

The creme of Example 3 was administered to 7 femal cancer patients who had developed a PPE on palm and/or plantar areas after 3 months of chemotherapy with epirubicin. The creme was administered to the concerned areas three days three times daily and the skin damages healed up completely within 3 days. In general, before each repeated administration of the creme the concerned areas have been cleaned with the cleansing milk of Example 6.

By comparison, three female cancer patients with PPE in the same areas after three months of chemotherapy received the creme of Example 3 without the microparticles (horny sponges) with the same treatment regimen. After 3 days an improvement was noted, the skin damages completely disappeared after 8 days.

Two female cancer patients with PPE in the same areas after three months of chemotherapy received the creme of Example 3 without free radical scavengers and without the microparticles with the same treatment regimen as described above. No improvement was noted up to 10 days of administration.

EXAMPLE 13

Protection of Alopecia

The permanent hair rinse of example 7 was administered to 5 female cancer patients who were treated with Taxol during a period of 3 months. Taxol was applied every 3 weeks.

The permanent hair rinse was administered on the scalp area two times daily—one day before and during the period of treatment of 3 months. Every fifth day the scalp was washed with the Shampoo of example 10.

During the first fife days after the Taxol treatment the hair pack II of Example 9 was applied in the evening.

Usually all patients lost their hairs during the first two weeks of the Taxol treatment.

In the present case the alopecia was reduced during the 3 months significantly. Even after 3 months of Taxol treatment ca 50% of the hairs remained on the scalp.

The invention claimed is:
1. A method for treating skin damage caused by chemotherapeutic treatment in a mammal in need thereof, wherein the skin damage is palmar-plantar erythrodysesthesia syndrome (PPE), comprising topically applying to affected skin of the mammal a therapeutically effective amount of a topical pharmaceutical composition comprising:

i.) free radical scavengers in an amount of 3-33% by weight based upon topical pharmaceutical composition total weight; and ii.) microparticles in an amount of 0.6 to 8% by weight based upon the topical pharmaceutical composition total weight, wherein the microparticales are carrier material, and wherein said microparticales have an average particle size ranging from 5 to 200 μmm, and wherein said microparticles are horny sponge, or a mixture of bamboo and kaolin;

wherein the free radical scavengers are selected from the group consisting of:
  (1) β-carotene;
  (2) a mixture of:
    a) a product obtained by enzymatic hydrolysis of an extract of *Querbracho blanco* bark, wherein the product contains at least 90% by weight of proanthocyanidin oligotners and a maximum of 10% by weight of gallic acid, wherein the product is present in an amount of 0.1 to 10% by weight relative to the total weight of the mixture;
    b) an extract of silkworm, wherein the extract of silkworm contains cecropine, amino acids and a vitamin mixture, wherein said extract of silkworm is present in an amount of 0.1 to 10% by weight relative to the total weight of the mixture;
    c) anon-ionic, cationic, or anionic hydrogel or combination thereof, wherein said hydrogel is present in an amount of 0.1 to 5% by weigh relative to the total weight of the mixture;
    d) one or more phospholipids in an amount of 0.1 to 30% by weight relative to the total weight of the mixture;
    e) an ultrasound decomposition product of baker's or brewer's yeast containing at least 150 units/ml superoxide dimutase in an amount of 0 to 4% by weight relative to the total weight of the mixture; and
    (f) water in an amount of up to 100% by weight relative to the total weight of the mixtu e; and
  (3) a combination of (1) and (2); and
wherein the topical pharmaceutical composition is administered prior to, during and/or after chemotherapeutic treatment with cytostatic agents.

2. The method of claim 1, wherein the free radical scavengers is (2).

3. The method of claim 1, wherein the free radical scavengers is (3) the combination of (1) and (2).

4. The method of claim 1, wherein the topical pharmaceutical composition is administered to skin or scalp in need thereof at least twice daily.

5. The method of claim 1, wherein the topical pharmaceutical composition is administered to skin and scalp in need thereof in an amount of at least 2 mg/cm².

6. The method of claim 1, wherein the topical pharmaceutical composition is a cream, lotion, ointment, gel or emulsion.

7. The method of claim 1, wherein the topical pharmaceutical composition further comprises pharmaceutically acceptable auxiliary agents.

8. The method of claim 1, wherein the topical pharmaceutical composition is administered 1 day prior to chemotherapeutic treatment, during chemotherapeutic treatment and at least 6 to 7 days after chemotherapeutic treatment.

9. The method of claim 4, wherein the topical pharmaceutical composition is administered to the skin in need thereof at least twice daily in an amount of at least 2 mg/cm².

10. The method of claim 1, wherein the administered topical pharmaceutic composition has a radical protection factor between 200 and 12000×1014 radicals per mg of the composition.

11. The method of claim 1, wherein the one or more free radical scavengers is (1) β-carotene.

* * * * *

UNITED STATES PATENT AND TRADEMARK OFFICE
CERTIFICATE OF CORRECTION

| | |
|---|---|
| PATENT NO. | : 9,446,084 B2 |
| APPLICATION NO. | : 13/035703 |
| DATED | : September 20, 2016 |
| INVENTOR(S) | : Golz-Berner et al. |

Page 1 of 2

It is certified that error appears in the above-identified patent and that said Letters Patent is hereby corrected as shown below:

On the Title Page

Item (30), in "Foreign Application Priority Data", in Column 1, Line 2, delete "10 2005 023 497" and insert --10 2005 023 497.6--, therefor Item (57), in "Abstract", in Column 2, Line 2, delete "amd" and insert --and--, therefor Item (57), in "Abstract", in Column 2, Line 4-5, delete "preaparation of a topuical pharmaceutical compostion" and insert --preparation of a topical pharmaceutical composition--, therefor Item (57), in "Abstract", in Column 2, Line 6, delete "buy" and insert --by--, therefor Item (57), in "Abstract", in Column 2, Line 7-8, delete "protextion or treatmnent" and insert --protection or treatment--, therefor Item (57), in "Abstract", in Column 2, Line 9, delete "protextion" and insert --protection--, therefor Item (57), in "Abstract", in Column 2, Line 12, before "free" delete "the", therefor In the Claims In Column 14, Line 6, in Claim 1, delete "microparticales" and insert --microparticles--, therefor In Column 14, Line 7, in Claim 1, delete "microparticales" and insert --microparticles--, therefor In Column 14, Line 8, in Claim 1, delete "µmm," and insert --µm,--, therefor In Column 14, Line 19, in Claim 1, delete "oligotners" and insert --oligomers--, therefor Signed and Sealed this
Fifth Day of June, 2018

Andrei Iancu
*Director of the United States Patent and Trademark Office*

CERTIFICATE OF CORRECTION (continued)
U.S. Pat. No. 9,446,084 B2

In Column 14, Line 28, in Claim 1, delete "anion-ionic," and insert --a non-ionic,--, therefor In Column 14, Line 37, in Claim 1, delete "dimutase" and insert --dismutase--, therefor In Column 14, Line 39, in Claim 1, delete "(f)" and insert --f)--, therefor In Column 14, Line 40, in Claim 1, delete "mixtu e;" and insert --mixture;--, therefor